United States Patent [19]

Blasius, Jr. et al.

[11] Patent Number: 4,795,421
[45] Date of Patent: Jan. 3, 1989

[54] ORAL HYGIENE SWAB

[75] Inventors: William G. Blasius, Jr., Higganum; Joseph F. Zygmont, Jr., Clinton, both of Conn.

[73] Assignee: Chesebrough-Pond's Inc., Greenwich, Conn.

[21] Appl. No.: 855,670

[22] Filed: Apr. 25, 1986

[51] Int. Cl.⁴ .............................................. A61F 13/00
[52] U.S. Cl. ...................................................... 604/1
[58] Field of Search ................... 604/1, 2; 433/229, 15

[56] References Cited

U.S. PATENT DOCUMENTS

| | | |
|---|---|---|
| 106,773 | 8/1870 | Blake . |
| 1,839,486 | 1/1932 | Lawton . |
| 2,218,738 | 10/1940 | Boysen ............................... 132/84 |
| 3,018,778 | 1/1962 | Brilliant ............................. 128/269 |
| 3,078,856 | 2/1963 | Bender et al. ....................... 132/93 |
| 3,139,094 | 6/1964 | Efeian ................................. 132/84 |
| 3,586,380 | 6/1971 | Allbeckoff ........................... 604/1 |
| 3,672,378 | 6/1972 | Silverman ........................... 132/93 |
| 4,033,365 | 7/1977 | Klepak ................................ 132/89 |
| 4,194,290 | 3/1980 | Vallhonrat ......................... 433/141 |
| 4,237,911 | 12/1980 | White ................................. 132/89 |
| 4,533,326 | 8/1985 | Anthony ............................ 433/229 |
| 4,576,190 | 3/1986 | Youssef .............................. 132/89 |

FOREIGN PATENT DOCUMENTS 1592513 7/1981 United Kingdom .

Primary Examiner—Robert Peshock
Attorney, Agent, or Firm—Melvin H. Kurtz

[57] ABSTRACT

The present invention is a mouth swab which comprises a support stick having a swab mounted on at least one end thereof. The swab is impregnated with an oral treatment composition (e.g., a mouth freshening composition) and is encapsulated with a dry, saliva-soluble polymeric coating. Placement of the swab in the mouth results in dissolution of the polymeric coating by the saliva in the mouth and allows for release of the oral treatment composition into the mouth cavity. In certain preferred embodiments the product can contain either a dental floss or toothpick implement within the support stick.

8 Claims, 1 Drawing Sheet

ORAL HYGIENE SWAB

BACKGROUND OF THE INVENTION

1. Field of the Invention

The present invention relates to an oral hygiene swab which contains an oral treatment solution. In an improved embodiment the product can also contain either a dental floss or toothpick implement to aid in the cleaning of the teeth.

2. Description of the Present Invention

U.S. Pat. No. 1,839,486 to J. A. Lawton illustrates a medicament carrier which comprises a number of braidable strands of a fiber or rubber which contain interstices in which a medicament or cleaning material can be placed. The interstices or pockets holding the material can be sealed by a suitable material, e.g., one which can be dissolved by the saliva. The carrier shown in this patent is not a swab-type product comprising an applicator stick having a swab mounted on at least one end thereof.

It is known to impregnate mouth swab products with suitable oral treatment solutions. Representative U.S. patents which describe such products include U.S. Pat. No. 3,018,778 to H. Brilliant, U.S. Pat. No. 3,078,856 to H. Bender et al., and U.S. Pat. No. 4,194,290 to O. D. Volhonrat. Such swab products need to be used within a very short period of time to prevent undesirable loss of the oral treatment composition if it is a liquid which can become dry upon being allowed to stand.

SUMMARY OF THE PRESENT INVENTION

The present mouth swab is an improved swab-type product which comprises a support stick having a swab mounted on at least one end thereof, the swab being impregnated with an oral treatment composition and being encapsulated with a dry, saliva-soluble polymeric coating.

The present invention has certain advantages from a commercial viewpoint. It can be designed as a disposable product. It is also lower in cost to fabricate than molded toothbrush products which might have a suitable oral treatment composition (e.g., toothpaste) placed in the brush portion of the product.

DESCRIPTION OF THE DRAWINGS

The present invention will be further understood by reference to the drawings which form a portion of the present specification and which form a part thereof wherein.

DETAILED DESCRIPTION OF THE PRESENT INVENTION

Figure 1:
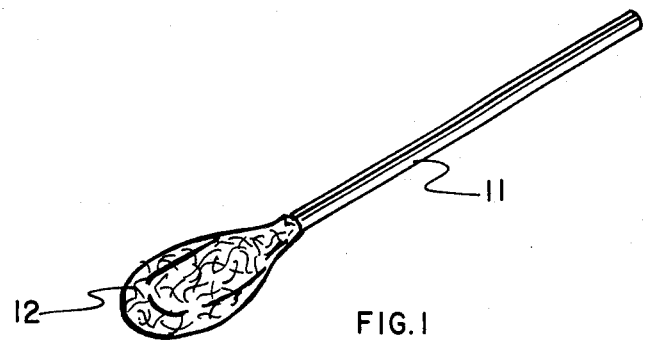
FIG. 1 is a perspective view showing the mouth swab of the present invention.

FIG. 1 shows the swab of the present invention in perspective view. It comprises a support stick 11 which can be formed of any suitable, durable and relatively rigid material such as wood, paper or plastic. In a preferred embodiment, it is formed of plastic and is hollow. Attached to at least one end of the support stick 11 is a swab 12 which is formed preferably of a suitable, absorbent material as is well known in the prior art. The swab is a non-woven structure comprising appropriate natural and/or synthetic fibers as is known in the swab art. Fine denier, nonabrasive fibrous materials are used in such swab products. Preferably, the swab 12 of the present invention is formed of a blend of cotton and polypropylene fibers as further illustrated in the Examples. In accordance with the present invention, the swab 12 is impregnated with a suitable oral treatment composition such as a liquid flavoring composition. The impregnated swab 12 is encapsulated with a dry, saliva-soluble polymeric coating 13 which is best seen in cross-sectional view in FIGS. 2 and 3. The terminology "oral treatment composition" is intended to be broadly construed as any composition which can be impregnated into swab 12 for later treatment of the oral cavity (teeth, gums, etc.) when the swab of the present invention is inserted into the mouth so that the saliva in the mouth acts upon and dissolves the polymeric coating 13. The polymeric coating is chosen so that it dissolves at weakly acidic to basic pH values (e.g., at pH values of about 5.5 or above) as is common in the oral cavity. Dissolution of coating 13 allows the saliva and impregnated swab to come in contact with one another to release the impregnated oral treatment composition into the mouth.

Figure 2:
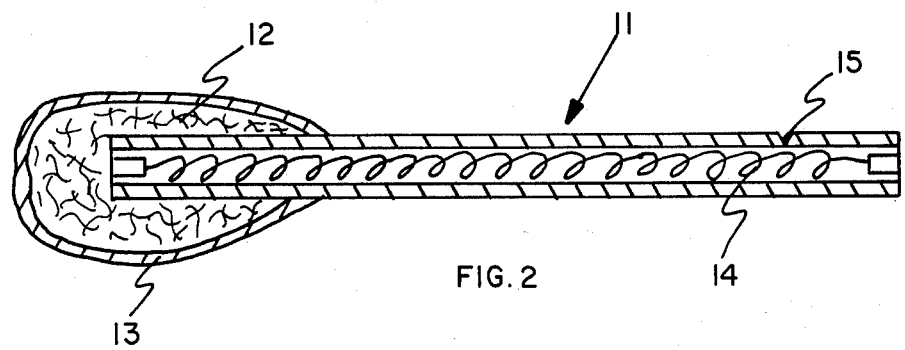
FIG. 2 is a view taken in cross-section showing an embodiment of the present swab with dental floss bonded to the inside of the swab support stick.

If desired, a length of dental floss 14 can be bonded inside the support stick 11 if it is made hollow. This is best shown in FIG. 2. A suitable score or notch 15 can be formed in the support stick 11 to allow for breaking of the stick. When this is done, the two parts of the broken support stick can be moved apart to allow for the dental floss to become exposed so that it can be utilized.

Figure 3:
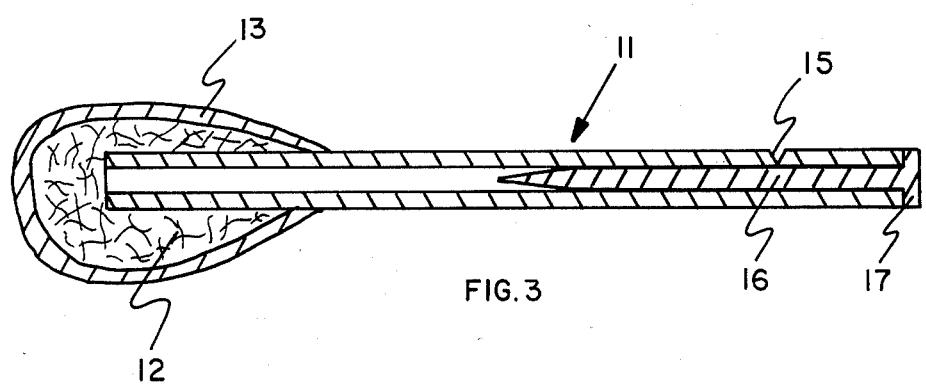
FIG. 3 is a cross-sectional view showing a toothpick stored inside the swab support stick.

FIG. 3 shows another embodiment of the present invention wherein a toothpick 16 is stored within the bore of hollow stick 11. A similar notch 15 is formed in the stick. The toothpick can have a flange 17 at one end to serve as a contact point with the end of the support stick and can be lightly glued thereto. A person desiring to remove the toothpick 16 merely needs to place their fingernail in the joint between support stick 11 and the flange 17 of the toothpick and pry the toothpick out of the support stick.

The present invention will be further understood by reference to the Examples which follow which describe certain embodiments in more detail.

EXAMPLE 1

This Example illustrates formation of a mouth swab containing dental floss in its support stick.

A blend of cotton and polypropylene fibers were formed into a cone-shaped swab in a mold on one end of a hollow polystyrene stick. A mixed spice mint flavor (1.5 cc) was injected into the fibers forming the swab. While the swab was still in the mold, an overcoat (1 cc) was applied to it. The overcoat composition comprised 100 parts by weight of acrylic resin (EUDRAGIT L30D brand from Rohm GmbH), 20 parts by weight of cellulose gum, 1% concentration (7H3SF from Hercules), 5 parts by weight of anhydrous aluminum silicate (KAOPOLITE 1168 brand), and 0.2 part by weight of sodium benzoate. After the coating had dried, the swab tip was ironed flat on two opposed sides to form a paddle-like swab tip. A length of dental floss was then glued to each end of the interior bore of the hollow stick.

EXAMPLE 2

This embodiment describes a formulation for the overcoat which is more abrasive than that described in Example 1. The overcoat was formed from the following ingredients:

| Ingredient | Parts by Weight |
| --- | --- |
| Acrylic resin (EUDRAGIT L30D brand) | 100 |
| Deionized water | 100 |
| Polyoxyethylene solution monostearate (TWEEN 60 brand from ICI) | 4 |
| Aluminum silicate (KAOPOLITE 1168 brand) | 25 |
| Siloxane antifoam (ANTIFOAM AF brand from Dow Corning) | 0.03 |

The overcoat was freeze dried for one hour.

EXAMPLE 3

This Example illustrates the ingredients used to form an alternate overcoat to those shown in earlier Examples.

| Ingredient | Parts by Weight |
| --- | --- |
| Acrylic resin (EUDRAGIT L30D brand) | 100 |
| Silica (CAB-O-SIL EH-5 brand) | 0.31 |
| Propylene glycol | 1.70 |
| Deionized water | 2.14 |

EXAMPLE 4

This Example describes an improved overcoat composition and describes a method of manufacture in which the flavoring in the swab does not coagulate the overcoat.

The ingredients used to form the overcoat were:

| Ingredient | Parts by Weight |
| --- | --- |
| Acrylic resin (EUDRAGIT L30D brand) | 100 |
| Silica (CAB-O-SIL M-5 brand) | 0.4 |
| Propylene glycol | 6.0 |
| Deionized water | 6.0 |

The method of manufacture comprised using only about three-quarters of the fiber normally present in the final swab to form a portion of the swab. The flavoring was then added to impregnate this portion of the swab. The remaining fiber was then wrapped over the flavor-impregnated portion of the swab and the overcoat was then applied.

EXAMPLE 5

This Example illustrates another, improved manufacturing process for making the swab of the present invention.

The fiber blend was applied to the stick and was formed using water. The tips were then ironed into a paddle-like shape. The flavor solution was applied to the tips and a spray coating of the overcoat from Example 4 was applied and allowed to dry.

EXAMPLE 6

This Example illustrates a quicker drying formulation and incorporated an encapsulated flavoring overcoat for more immediate taste sensation.

The overcoat formulation was formed from:

| Ingredient | Parts by Weight |
| --- | --- |
| Ethyl alcohol | 150 |
| Acrylic resin (CARBOSET 525 brand from Goodrich) | 15 |

The encapsulated flavoring overcoat was formed by dusting an encapsulated flavoring additive (No. 135-40001 from International Flavors & Fragrances) over the still tacky overcoat.

EXAMPLE 7

This Example describes the specifications for a particularly preferred embodiment of the present invention.

The stick is formed of white polystyrene and has a length of 4.125 inches. It has an outside diameter of 0.110 inch.

The fiber used to form the swab is a blend of 85% cotton fibers and 15% polypropylene fibers. The amount used to form the swab tip is 130 mg. The solution used in forming the swab tip is a 0.25% aqueous solution of methylcellulose (METHOCEL E15-LV PREMIUM brand from Dow Chemical). The dimensions of the paddle-like swab are: 0.4 inch in length; 0.72 inch in width; and 0.20 inch in thickness.

The flavor mixture used is: 38.4 parts of minty spice (from Noville Inc.); 19.2 parts of spice mint (from Noville Inc.); 38.4 parts of 67 Saccharine (from Noville Inc.); and 3.8 parts of $TiO_2$.

The overcoat formulation comprises: 100 parts by weight of acrylic resin (EUDRAGIT L30D brand); 200 parts of deionized water; 6 parts of propylene glycol; 0.6 part of silica (CAB-O-SIL M-5 brand); 0.6 part of magnesium aluminum silicate (VAN GEL ES brand); and 0.1 part of potassium sorbate. The swab tip was dipped into this overcoat rather than having the overcoat sprayed onto the tip. The encapsulated flavor additive used in Example 6 was dusted over the overcoat while it was still tacky.

The foregoing Examples are intended to describe certain embodiments of the present invention and are not intended to be construed in a limiting sense. The scope of protection that is sought is set forth in the claims which follow.

What is claimed:

1. A mouth swab comprising a support stick having a swab mounted on at least one end thereof, the swab being impregnated with an oral solution and being encapsulated with a dry, saliva-soluble polymeric coating.

2. A swab as claimed in claim 1 which has one swab tip.

3. A swab as claimed in claim 1 wherein the coating comprises an acrylic resin.

4. A swab as claimed in claim 1 which has a hollow support stick.

5. A swab as claimed in claim 4 which has a length of dental floss bonded inside the support stick.

6. A swab as claimed in claim 4 which has a toothpick stored inside the support stick.

7. A swab as claimed in claim 5 which has one swab tip and wherein the coating comprises an acrylic resin.

8. A swab as claimed in claim 6 which has one swab tip and wherein the coating comprises an acrylic resin.

* * * * *